USO08552382B2

(12) United States Patent
Shelley et al.

(10) Patent No.: US 8,552,382 B2
(45) Date of Patent: Oct. 8, 2013

(54) THERMAL EFFECT MEASUREMENT WITH MID-INFRARED SPECTROSCOPY (75) Inventors: Paul H. Shelley, Lakewood, WA (US); Gregory J. Werner, Puyallup, WA (US); Paul G. Vahey, Seattle, WA (US)

(73) Assignee: The Boeing Company, Chicago, IL (US)

( * ) Notice: Subject to any disclaimer, the term of this patent is extended or adjusted under 35 U.S.C. 154(b) by 230 days.

(21) Appl. No.: 12/164,023

(22) Filed: Aug. 14, 2008

(65) Prior Publication Data
US 2010/0038544 A1 Feb. 18, 2010

(51) Int. Cl.
G01J 3/42 (2006.01)
G01J 3/453 (2006.01)

(52) U.S. Cl.
USPC ............... 250/339.09; 250/339.12; 250/341.8

(58) Field of Classification Search
USPC .............................. 250/339.12, 341.8, 339.09
See application file for complete search history.

(56) References Cited

U.S. PATENT DOCUMENTS

| 4,483,629 | A | 11/1984 | Schwarz et al. |
| 5,209,569 | A | 5/1993 | Fujiwara et al. |
| 5,638,284 | A | 6/1997 | Helmer et al. |
| 5,945,676 | A | 8/1999 | Khalil et al. |
| 5,965,888 | A | 10/1999 | Engstrom et al. |
| 6,434,267 | B1 | 8/2002 | Smith |
| 6,495,833 | B1 | 12/2002 | Alfano et al. |
| 6,623,159 | B2 | 9/2003 | Takahara et al. |
| 7,064,331 | B2 | 6/2006 | Rothenfusser et al. |
| 7,897,923 | B2 | 3/2011 | Shelley et al. |
| 2002/0107644 | A1 | 8/2002 | Meglen et al. |
| 2002/0109093 | A1 | 8/2002 | Kelley |
| 2002/0113212 | A1* | 8/2002 | Meglen et al. ........... 250/339.05 |
| 2002/0167988 | A1 | 11/2002 | Zhu |
| 2004/0155190 | A1 | 8/2004 | Shelley et al. |
| 2004/0159789 | A1 | 8/2004 | Treado et al. |
| 2005/0067569 | A1* | 3/2005 | Shelley et al. ............. 250/341.8 |
| 2006/0047444 | A1* | 3/2006 | Brown et al. .................. 702/30 |
| 2007/0009009 | A1 | 1/2007 | Dziki |
| 2007/0131862 | A1* | 6/2007 | Cowan et al. ............ 250/339.09 |
| 2009/0321647 | A1 | 12/2009 | Shelley et al. |
| 2009/0321648 | A1 | 12/2009 | Shelley et al. |
| 2009/0323757 | A1 | 12/2009 | Werner et al. |
| 2010/0038544 | A1 | 2/2010 | Shelley et al. |

FOREIGN PATENT DOCUMENTS

| EP | 11 15 0399 | 4/2001 |
| EP | 2138829 A1 | 12/2009 |
| EP | 2138830 A2 | 12/2009 |
| WO | WO2008048705 A2 | 4/2008 |

OTHER PUBLICATIONS

Extended Search Report for EP Application No. 09251357.1 dated Oct. 9, 2009.

(Continued)

Primary Examiner — Walter L Lindsay, Jr.
Assistant Examiner — Jessica L Eley
(74) Attorney, Agent, or Firm — Parsons Behle & Latimer (57) ABSTRACT A method of determining a physical property of a composite material includes providing a series of composite materials/surfacing films, which are subjected to increasing thermal experience to create a set of thermal effect standards, collecting mid-IR spectra on those standards, performing data pre-processing and then multivariate calibration on the spectra of the composite materials/surfacing films, and using that calibration to predict the thermal effect for samples in question.

20 Claims, 5 Drawing Sheets

(56) References Cited

OTHER PUBLICATIONS

Extended Search Report for EP Application No. 1150399.1 dated Apr. 20, 2011.
19941.053US02_Adamson "Chemical surface Characterization and depth profiling of automotive coating systems"_Prog. Polym. Sci. 25 (2000) 1363-1409.
19941.053US02_Gerlock_On the use of Fourier transform infared spectroscopy and ultraviolet spectroscopy to assess the weathering performance of isolated clearcoats from different chemical families_ Polymer Degradation and Stability 62 (1998) 225-234.
19941_053US02_Office Action issued Jul. 16, 2012 in U.S. Appl. No. 12/684,368.
Janke et al (1993); "Composite Heat Damage Assesment;" OSTI ID: 245551, p. 1-16.
Fisher et al; (1995); "Non Destructive Inspection of Graphite-Epoxy Compsites for Heat Damage Using Laser-Induced Fluorescence." Applied Spectroscopy 46 (9); pp. 1225-1231.
Amin, M.B., Hamid, S.H., and Rahman, F.; (1995), Prediction of mechanical properties of weather-induced degraded plastics in Saudi Arabia. Journal of Applied Polymer Science, 56: 279-284.
Hamid, S.H. (2000), Ultraviolet-induced degradation of Ziegler-Natta and metallocene catalyzed polyethylenes; Journal of Applied Polymer Science, 78: 1591-1596.
Lemaire, J. et al; Prediction of Coating Lifetime Based on FTIR Microspectrophotometric Analysis of Chemical Evolutions; Apr. 15, 1999; American Chemical Society, 246-256.
US Patent and Trademark Office; Non-Final Office Action for U.S. Appl. No. 12/164,025 dated Mar. 25, 2010.
US Patent and Trademark Office; Final Office Action for U.S. Appl. No. 12/164,025 dated Sep. 1, 2010.
US Patent and Trademark Office; Non-Final Office Action for U.S. Appl. No. 12/164,026 dated Sep. 28, 2010.
US Patent and Trademark Office; Final Office Action for U.S. Appl. No. 12/164,026 dated Mar. 29, 2010.
United States Patent and Trademark Office; Office Action issued Dec. 12, 2011 in U.S. Appl. No. 12/684,368.
US Patent and Trademark Office; Non-Final Office Action for U.S. Appl. No. 12/164,022 dated May 27, 2011.
US Patent and Trademark Office; Office Action Dated Oct. 1, 2012 for U.S. Appl. No. 12/164,017.

* cited by examiner

THERMAL EFFECT MEASUREMENT WITH MID-INFRARED SPECTROSCOPY

CROSS REFERENCE TO RELATED APPLICATIONS

This application is related to U.S. patent application Ser. No. 12/164,025 filed Jun. 28, 2008, now U.S. Pat. No. 7,897,923, U.S. patent application Ser. No. 12/164,026 filed Jun. 28, 2008, now U.S. Pat. No. 7,919,753, U.S. patent application Ser. No. 12/164,022 filed Jun. 28, 2008, now U.S. Pat. No. 8,083,399, and U.S. patent application Ser. No. 12/164,017 filed Jun. 28, 2008, all filed concurrently herewith on Jun. 28, 2008, each of which applications is incorporated by reference herein in its entirety.

FIELD OF THE INVENTION

The disclosure relates to methods for determining thermal effect in composite materials. More particularly, the disclosure relates to a method for accurately assessing thermal effect in a composite material or surfacing film using mid-infrared spectroscopy.

BACKGROUND OF THE INVENTION

Resin-fiber composite materials are utilized in a variety of applications including the aerospace industry, for example. Structures which are constructed of resin-fiber composite materials may be exposed to heat, which may affect the composite materials in various ways. These heat-induced effects may include chemical effect in which changes such as oxidation, material loss and the breaking and/or forming of chemical bonds occurs in the polymer chemical structure of the composite materials. Resin decomposition, strength effect, charring and fiber decomposition of the composite materials may occur at increasing temperatures.

Composite materials and epoxy-based surfacing films are typically cured under a vacuum at 250-350° F. for several hours. Repairs to the composite materials or surfacing films can become necessary if voids are found during an NDI inspection or if a flaw is found. These repairs may require the use of heating blankets that are notorious for having hot spots. Thus, during the repair some areas of the composite material or surfacing film may become overheated; in the case of epoxy-based surfacing films, a color change (dark or blackened) may be noticeable. Thermal effect for in-service airplanes can occur from engine and run-way fires, electrical problems, lightening strikes, and other causes. Thermal effect may affect the mechanical and structural integrity of composite materials and surfacing films.

Repair or removal of heat-effected composite materials or surfacing films on a structure may involve first determining the degree of harmful heat effect to the composite materials or surfacing films. Although determining the degree of heat effect to composite materials or surfacing films may be performed by visual inspection, heat effect may not be visually apparent. Previous methods of determining the presence and extent of heat effect in composite materials and surfacing films includes obtaining an infrared spectrum of a heat-affected composite standard and correlating the infrared spectrum obtained from the composite standard with the degree of thermal effect of the composite standard. An infrared spectrum obtained from the composite material or surfacing film the heat effect of which is in question can then be compared to the infrared spectrum obtained from the composite standard to determine the presence and assess the degree of thermal effect in the composite material or surfacing film. Current methods of determining the presence and extent of heat effect in composite materials and surfacing films include obtaining the spectra of a series of heat-affected composite standards and building a multivariate model with the spectra of those standards. An infrared spectrum obtained from the composite material or surfacing film which is in question can then be predicted by the multivariate model to determine the presence and assess the degree of thermal effect in the composite material or surfacing film.

U.S. Pat. No. 7,115,869 discloses a method for measurement of composite heat effect with infrared spectroscopy by which an amount of heat exposure to a resin-fiber composite substrate is determined. According to the method, a value of infrared energy reflected by a composite substrate is determined. The value of infrared energy which is reflected or absorbed is correlated to a degree or amount of heat exposure of the composite substrate. The thermal effect measurement method of the present disclosure is more sensitive than that which is disclosed in U.S. Pat. No. 7,115,869 and is richer in spectral detail, providing a better indication of whether thermal effect has occurred in a composite material as well as the extent of effect. Moreover, the method can be implemented using a hand-held spectrometer which facilitates convenience and flexibility in measuring the possibility or degree of thermal effect in the composite material in question.

Calibration of infrared spectrometers to residual strength in composite materials or surfacing films correlates the resin condition as read from the infrared spectrum to the residual strength of the material or film which degrades as the resin degrades with progressively increasing temperatures. Therefore, the infrared sensors may be calibrated using time-controlled thermal soak standards which are obtained by exposing various composite materials or surfacing film controls to various temperatures for a particular time period such as one hour, for example. One method of preparing the standards includes placing the standards in an oven which is calibrated periodically and monitored continuously using multiple thermocouples as the composite materials are thermally exposed. Furthermore, thermal effect to composite materials or surfacing films may not follow a linear course. The most useful parameters for thermal effect are those that the repair process person can understand and use as criteria for removal of effect material. Under circumstances in which it is desirable to remove all weakened material, a measure of the residual strength in the material is best. Multivariate calibration allows calibration to such physical properties under circumstances in which previous calibration methods were insufficient.

Therefore, a method for accurately assessing thermal effect in a composite material or surfacing film using mid-infrared spectroscopy is needed.

SUMMARY OF THE INVENTION

The disclosure is further generally directed to a method of determining a physical property of a composite material. An illustrative embodiment of the method includes providing a series of composite material standards with increasing thermal exposure (with or without a surfacing film), irradiating the composite material standards and/or the surfacing films with mid-spectrum infrared energy, detecting infrared energy reflected from the composite material standards/surfacing films, performing multivariate calibration on the series of the infrared spectra reflected from the composite material standards/surfacing films, performing a multivariate calibration to the infrared spectra from the standards to make a model of the spectral changes with increasing thermal exposure (or decreasing mechanical properties), and using the multivariate model to predict the thermal exposure or mechanical properties of composite materials in question.

BRIEF DESCRIPTION OF THE ILLUSTRATIONS

DETAILED DESCRIPTION OF THE PREFERRED EMBODIMENT

Figure 1:
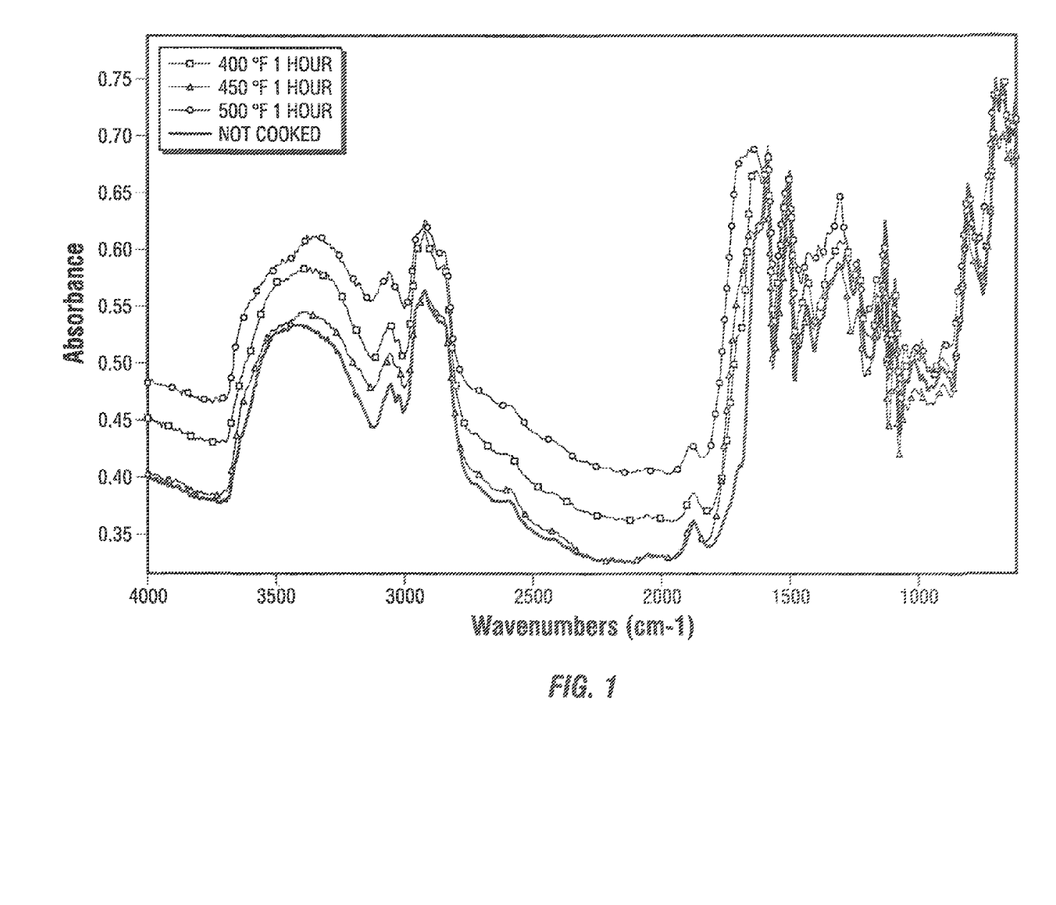
FIG. 1 is a series of mid-IR spectra on thermally exposed graphite composite (CFRP) standards which were exposed for 1 hour each at 400, 450 and 500° F. and no thermal exposure, respectively.
Figure 2:
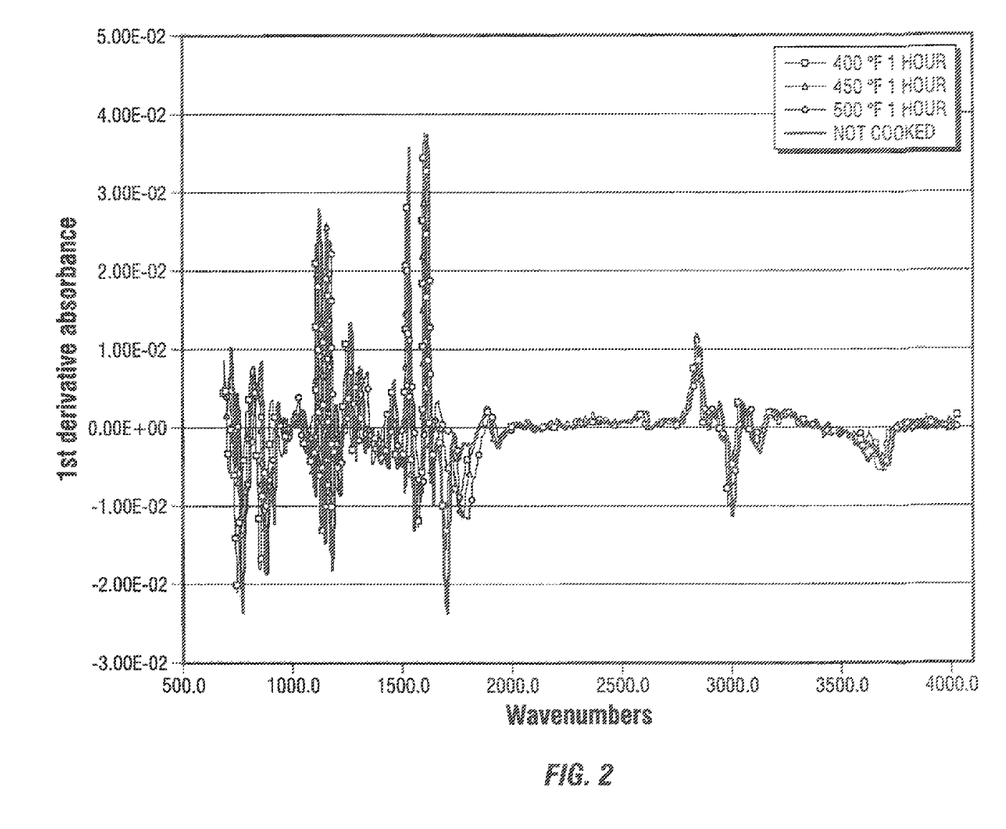
FIG. 2 is a the same series of mid-IR spectra from FIG. 1 but with first derivative and 7 point smoothing pre-processing with the Savitzky Golay method.

Referring initially to FIGS. 1-4, an illustrative embodiment of a method of multivariate calibration for thermal effect with mid-IR spectra is shown. As shown in block 402 of flow diagram 400 in FIG. 4, the thermal effect calibration begins with providing CFRP (carbon fiber reinforced polymer) standards that are carefully cooked using carefully-controlled thermal exposure information in a range of interest and then tested to obtain residual mechanical properties data. Block 404 shows the mid-IR spectral data collection step in which infrared spectra may be collected on the standards with one or more spectra on each standard. In some applications, a hand-held spectrometer may be used to measure the spectral properties of the material in question. The raw infrared spectra obtained for the standards are shown in FIG. 1. Block 406 shows the data pre-processing step and FIG. 2 shows the results of a typical pre-processing method.

Figure 3:
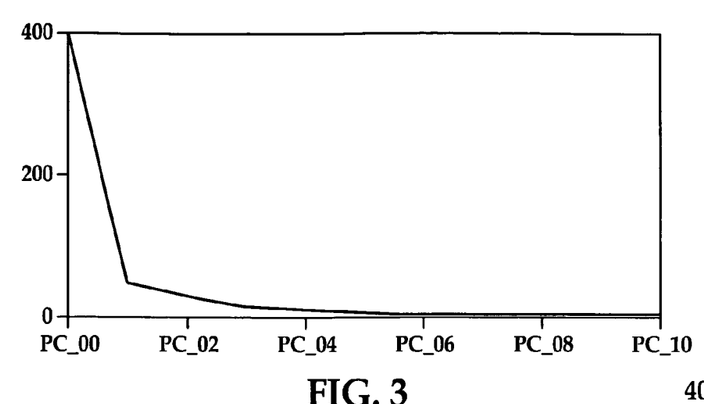
FIG. 3 is the regression vector from the multivariate calibration of the mid-IR spectra to the un-notched compression test stress results of the standards using the PLS (partial least squares) multivariate calibration method.
Figure 4:
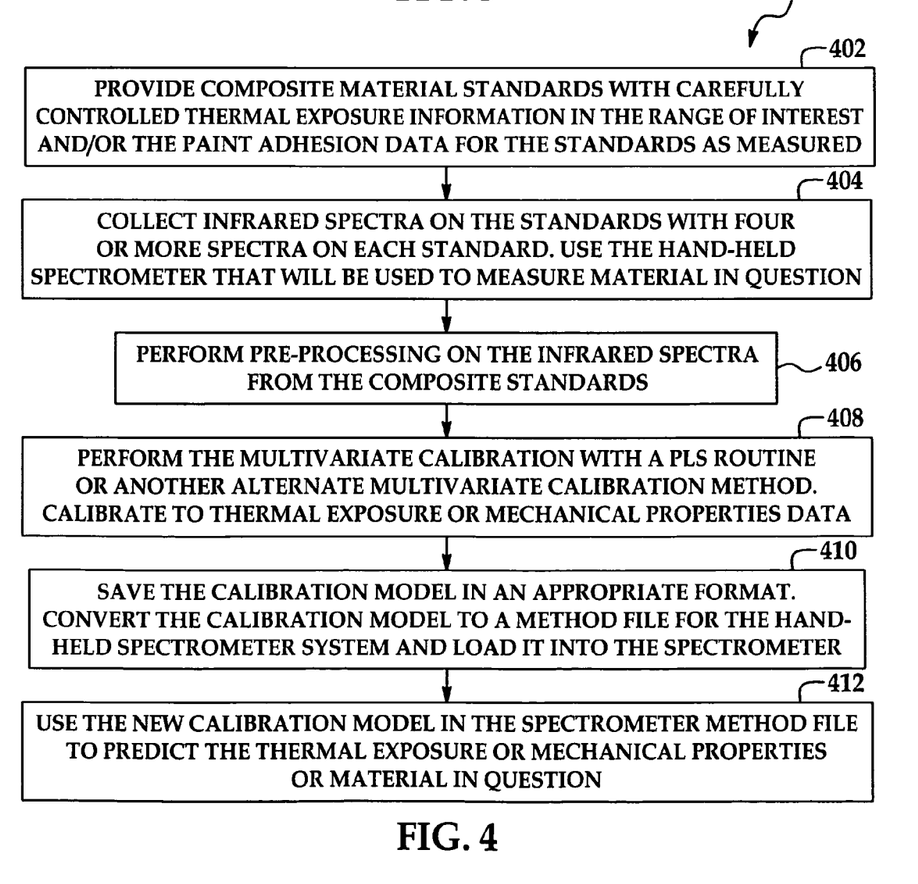
FIG. 4 is a flow diagram which illustrates the multivariate calibration and prediction method.

Block 408 shows the multivariate calibration step which may be carried out using a PLS routine or an alternative multivariate calibration method. Calibration of the multivariate calibration to thermal exposure or mechanical properties data for a composite material is obtained. FIG. 3 shows the regression coefficients that result from that calibration. Block 410 shows the step where the multivariate calibration is saved in an appropriate format, converted into a method file and then loaded into the hand-held mid-IR device that will be used to read thermal effect on the CFRP material in question. Block 412 shows the CFRP material in question being predicted for residual stress values that would indicate the extent of thermal effect in the material in question using the new calibration model in the spectrometer method file. If the original standards are predicted here, an accuracy figure for the methods based on the difference between the known stress numbers and those predicted by the method just developed can be obtained.

Figure 4A:
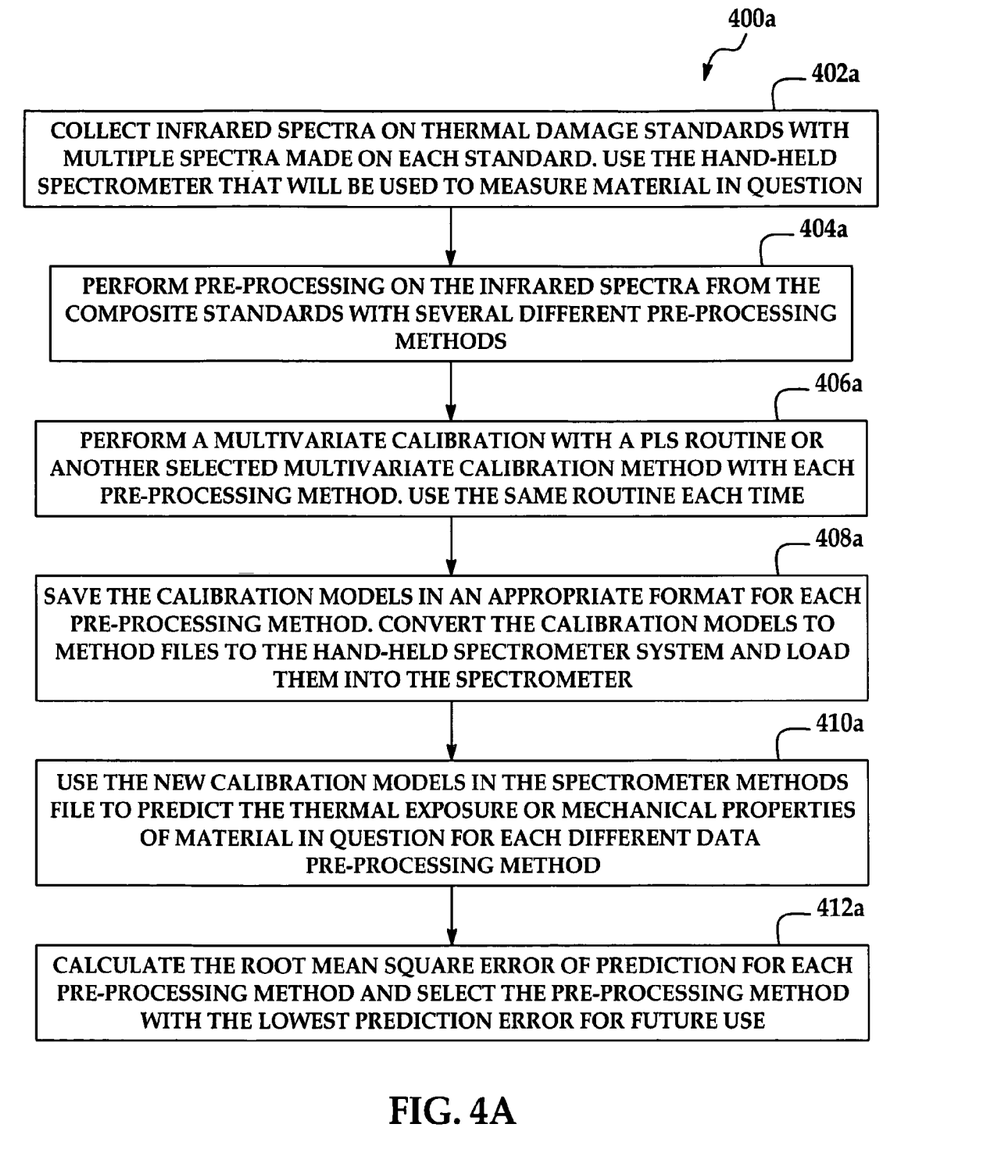
FIG. 4A is a flow diagram which illustrates important points in the multivariate calibration method.

Referring next to FIG. 4A, a flow diagram 400a which illustrates an illustrative embodiment of a method of optimizing the data pre-processing method for CFRP thermal effect calibration with multivariate methods is shown. In block 402a, a thermal effect standard is provided. The thermal effect standard may have been fabricated according to the method which was heretofore described with respect to the flow diagram 400 in FIG. 4. Infrared spectra on the thermal effect standards are collected, with multiple spectra obtained on each standard. A hand-held spectrometer which will be used to measure the material in question may be used. In block 404a, the infrared spectra of the thermal effect standards are made using the mid-IR wavelength range of from about 2.5 μm to about 15 μm. Pre-processing on the infrared spectra from the composite standards may be made using may be made using several different pre-processing methods. In block 406a, a multivariate calibration with a PLS routine or other multivariate calibration method may be performed with each pre-processing method. In block 408a, the calibration methods may be saved in an appropriate format for each pre-processing method. The calibration models may be converted to method files which are compatible with the hand-held spectrometer system, and then the method files loaded into the spectrometer. In block 410a, the new calibration models in the spectrometer methods file may be used to predict the thermal exposure or mechanical properties of the material in question for each different data pre-processing method. In block 412a, the root mean square error of prediction for each pre-processing method is calculated. The pre-processing method having the lowest prediction error may be selected for future use. FIG. 3 illustrates the regression vector from the multivariate calibration of the mid-IR spectra to the un-notched compression test stress results of the standards using the PLS (partial least squares) multivariate calibration method.

Figure 5:
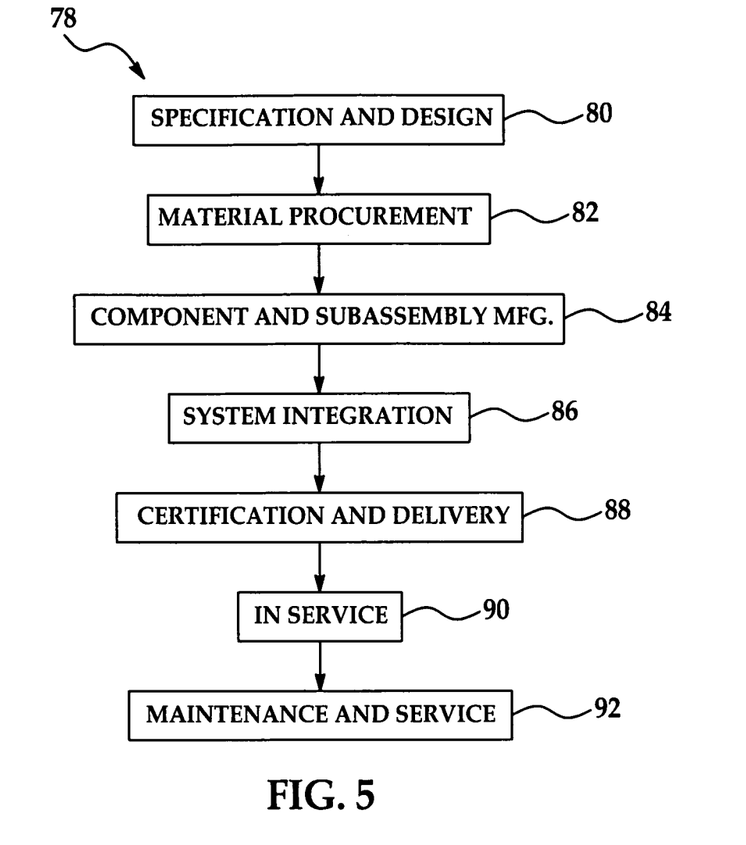
FIG. 5 is a flow diagram of an aircraft production and service methodology.
Figure 6:
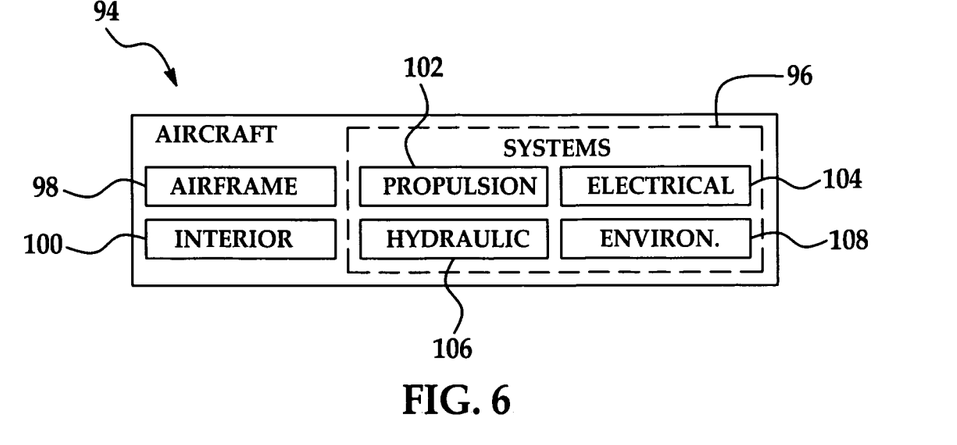
FIG. 6 is a block diagram of an aircraft.

Referring next to FIGS. 5 and 6, embodiments of the disclosure may be used in the context of an aircraft manufacturing and service method 78 as shown in FIG. 5 and an aircraft 94 as shown in FIG. 6. During pre-production, exemplary method 78 may include specification and design 80 of the aircraft 94 and material procurement 82. During production, component and subassembly manufacturing 84 and system integration 86 of the aircraft 94 takes place. Thereafter, the aircraft 94 may go through certification and delivery 88 in order to be placed in service 90. While in service by a customer, the aircraft 94 may be scheduled for routine maintenance and service 92 (which may also include modification, reconfiguration, refurbishment, and so on).

Each of the processes of method 78 may be performed or carried out by a system integrator, a third party, and/or an operator (e.g., a customer). For the purposes of this description, a system integrator may include without limitation any number of aircraft manufacturers and major-system subcontractors; a third party may include without limitation any number of vendors, subcontractors, and suppliers; and an operator may be an airline, leasing company, military entity, service organization, and so on.

As shown in FIG. 6, the aircraft 94 produced by exemplary method 78 may include an airframe 98 with a plurality of systems 96 and an interior 100. Examples of high-level systems 96 include one or more of a propulsion system 102, an electrical system 104, a hydraulic system 106, and an environmental system 108. Any number of other systems may be included. Although an aerospace example is shown, the principles of the invention may be applied to other industries, such as the automotive industry.

The apparatus embodied herein may be employed during any one or more of the stages of the production and service method 78. For example, components or subassemblies corresponding to production process 84 may be fabricated or manufactured in a manner similar to components or subassemblies produced while the aircraft 94 is in service. Also, one or more apparatus embodiments may be utilized during the production stages 84 and 86, for example, by substantially expediting assembly of or reducing the cost of an aircraft 94. Similarly, one or more apparatus embodiments may be utilized while the aircraft 94 is in service, for example and without limitation, to maintenance and service 92.

Although the embodiments of this disclosure have been described with respect to certain exemplary embodiments, it is to be understood that the specific embodiments are for purposes of illustration and not limitation, as other variations will occur to those of skill in the art.

What is claimed is:

1. An infrared spectroscopy multivariate calibration and prediction method, comprising:
    providing resin-fiber polymer composite material standards with physical properties information as a function of thermal exposure in a range of interest;
    collecting infrared data comprising mid-infrared spectra on said composite material standards;
    performing multivariate calibration on said infrared data including all wavelengths comprising said mid-infrared spectra;
    defining a calibration model by calibrating said multivariate calibration on said infrared data to said physical properties information; and
    predicting physical properties comprising a physical property value of a resin-fiber polymer composite material in question using said calibration model.

2. The method of claim 1 wherein said collecting infrared spectra on each of said composite material standards comprises collecting at least four infrared spectra on each of said composite material standards.

3. The method of claim 1 further comprising providing a spectrometer and loading said calibration model into said spectrometer and wherein said predicting physical properties of a composite material in question using said calibration model comprises predicting physical properties of a composite material in question by operation of said spectrometer.

4. The method of claim 3 wherein said providing a spectrometer comprises providing a hand-held spectrometer.

5. The method of claim 4 wherein said collecting infrared data on said composite material standards comprises collecting infrared data on said composite material standards using said hand-held spectrometer.

6. The method of claim 1 wherein said providing composite material standards with physical properties information in a range of interest comprises providing composite material standards with thermal exposure properties information in a range of interest.

7. The method of claim 1 wherein said providing composite material standards with physical properties information in a range of interest comprises providing composite material standards with mechanical properties in a range of interest.

8. A method of determining a physical property of a composite material by infrared spectroscopy, comprising:
    providing resin-fiber polymer composite material standards with physical properties as a function of thermal exposure information in a range of interest;
    collecting infrared data comprising mid-infrared spectra on said composite material standards;
    performing pre-processing on said infrared data;
    performing multivariate calibration on said infrared data including all wavelengths comprising said mid-infrared spectra;
    defining a calibration model by calibrating said multivariate calibration on said infrared data to said physical properties information; and
    predicting physical properties comprising a physical property value of a resin-fiber polymer composite material in question using said calibration model.

9. The method of claim 8 wherein said collecting infrared spectra on each of said composite material standards comprises collecting at least four infrared spectra on each of said composite material standards.

10. The method of claim 8 further comprising providing a spectrometer and loading said calibration model into said spectrometer and wherein said predicting physical properties of a composite material in question using said calibration model comprises predicting physical properties of a composite material in question by operation of said spectrometer.

11. The method of claim 10 wherein said providing a spectrometer comprises providing a hand-held spectrometer.

12. The method of claim 11 wherein said collecting infrared data on said composite material standards comprises collecting infrared data on said composite material standards using said hand-held spectrometer.

13. The method of claim 8 wherein said providing composite material standards with physical properties information in a range of interest comprises providing composite material standards with residual strength properties as a function of thermal exposure information in a range of interest.

14. The method of claim 8 wherein said providing composite material standards with physical properties information in a range of interest comprises providing composite material standards with mechanical properties as a function of thermal exposure in a range of interest.

15. A method of determining a physical property of a composite material by infrared spectroscopy, comprising:
    providing resin-fiber polymer composite material thermal effect standards with physical properties as a function of thermal exposure information in a range of interest;
    collecting mid-infrared spectra on said composite material thermal effect standards;
    performing pre-processing on said infrared spectra using various pre-processing methods;
    performing multivariate calibration on said infrared spectra including all wavelengths comprising said mid-infrared spectra;
    defining calibration models by calibrating said multivariate calibration on said mid-infrared spectra to said physical properties information;
    saving said calibration models in an appropriate format for each of said pre-processing methods;
    converting said calibration models to spectrometer method files;
    providing a spectrometer;
    loading said spectrometer method files into said spectrometer;
    and predicting physical properties comprising a physical property value of a resin-fiber polymer composite material in question for each of said pre-processing methods using said calibration models in said spectrometer method files.

16. The method of claim 15 wherein said collecting infrared spectra on said composite material thermal effect standards comprises collecting at least four infrared spectra on each of said composite material thermal effect standards.

17. The method of claim 15 wherein said providing composite material thermal effect standards with physical properties information in a range of interest comprises providing composite material effect standards with mechanical properties information as a function of thermal exposure in a range of interest.

18. The method of claim 15 wherein said providing a spectrometer comprises providing a hand-held spectrometer.

19. An infrared spectroscopy multivariate calibration and prediction method, comprising:
providing resin-fiber polymer composite material standards with mechanical properties information as a function of thermal exposure in a range of interest;
collecting at least four mid-infrared spectra on each of said composite material standards;
performing pre-processing on said infrared spectra;
performing multivariate calibration on said infrared spectra including all wavelengths comprising said spectra;
defining a calibration model by calibrating said multivariate calibration on said infrared spectra to said mechanical properties information;
saving said calibration model in an appropriate format;
converting said calibration model to a method file for a hand-held spectrometer;
loading said calibration model into said hand-held spectrometer; and
predicting a mechanical property value of a resin-fiber polymer composite material in question using said hand-held spectrometer.

20. A method of determining a physical property of a composite material by infrared spectroscopy, comprising:
providing resin-fiber polymer composite material thermal effect standards with thermal mechanical properties information as a function of thermal exposure in a range of interest;
providing a hand-held spectrometer;
collecting multiple mid-infrared spectra on each of said composite material thermal effect standards using said hand-held spectrometer;
performing pre-processing on said infrared spectra using various pre-processing methods;
performing multivariate calibration on said infrared spectra including all wavelengths comprising said spectra;
defining calibration models by calibrating said multivariate calibration on said infrared spectra to said mechanical properties information;
saving said calibration models in an appropriate format for each of said pre-processing methods;
converting said calibration models to spectrometer method files for said hand-held spectrometer;
loading said spectrometer method files into said hand-held spectrometer;
predicting a mechanical property value of a resin-fiber polymer composite material in question for each of said pre-processing methods using said calibration models in said spectrometer method files;
calculating the mean root square error of prediction for each of said pre-processing methods; and
selecting a pre-processing method having the lowest prediction error for future use.

* * * * *